United States Patent
Klein Woolthuis

(10) Patent No.: US 9,452,111 B2
(45) Date of Patent: Sep. 27, 2016

(54) DENTAL IMPLANT SYSTEM AND ASSOCIATED INSERTION INSTRUMENTS

(75) Inventor: Harmen Frederik Klein Woolthuis, Baarn (NL)

(73) Assignee: WHITE IMPLANTS DEVELOPMENT CORP., Amsterdam (NL)

( * ) Notice: Subject to any disclaimer, the term of this patent is extended or adjusted under 35 U.S.C. 154(b) by 267 days.

(21) Appl. No.: 14/006,541

(22) PCT Filed: Mar. 19, 2012

(86) PCT No.: PCT/NL2012/050168
§ 371 (c)(1),
(2), (4) Date: Jan. 7, 2014

(87) PCT Pub. No.: WO2012/128623
PCT Pub. Date: Sep. 27, 2012

(65) Prior Publication Data
US 2014/0113249 A1    Apr. 24, 2014

(30) Foreign Application Priority Data
Mar. 21, 2011   (NL) ..................................... 2006435

(51) Int. Cl.
*A61C 8/00*    (2006.01)
*A61K 6/04*    (2006.01)

(52) U.S. Cl.
CPC .............. *A61K 6/04* (2013.01); *A61C 8/0012* (2013.01); *A61C 8/0022* (2013.01); *A61C 8/0066* (2013.01); *A61C 8/0089* (2013.01)

(58) Field of Classification Search
CPC  A61C 8/0089;  A61C 8/0022;  A61C 8/0066;  A61C 8/0012
See application file for complete search history.

(56) References Cited

U.S. PATENT DOCUMENTS

| 6,247,932 | B1 * | 6/2001 | Sutter ................. | A61C 8/0087 206/368 |
| 6,416,324 | B1 | 7/2002 | Day | |
| 8,469,710 | B2 * | 6/2013 | Bondar ................ | A61C 8/0001 433/141 |
| 8,951,043 | B2 * | 2/2015 | Beekmans ........... | A61C 8/0022 433/173 |
| 2002/0150862 | A1 | 10/2002 | Day | |
| 2011/0212417 | A1 | 9/2011 | Beekmans | |

FOREIGN PATENT DOCUMENTS

WO   2010 053352   5/2010

OTHER PUBLICATIONS

International Search Report Issued Sep. 12, 2012 in PCT/NL12/050168 Filed Mar. 19, 2012.

* cited by examiner

*Primary Examiner* — Ralph Lewis
(74) *Attorney, Agent, or Firm* — Oblon, McClelland, Maier & Neustadt, L.L.P.

(57) ABSTRACT

An implant system including: an insertion part including a screw part and neck part including a recess in a neck end face thereof for fixing an abutment and, distanced from the neck end face, projections; an insertion instrument screwing down the insertion part, and including a handle part and socket part having a socket end face including an opening and at least a driving part laterally bounded by walls, which driving part has a cross-section at right angles to the longitudinal axis, to accommodate the neck part and transfer tightening torque to the insertion part through the projections, the opening including a bridge part contiguous to the driving part and enclosing the neck part, situated next to the projections and extending to the neck end face, to form an interspace between the bridge part and the neck part, when the driving part embraces the projections of the neck part.

6 Claims, 3 Drawing Sheets

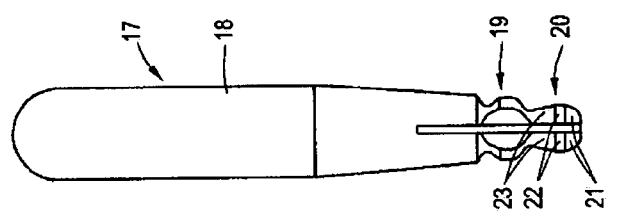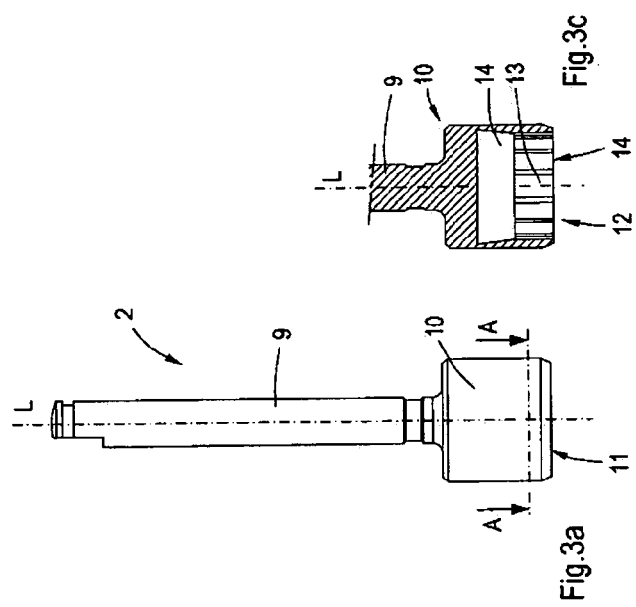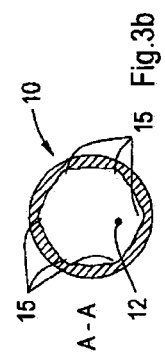

DENTAL IMPLANT SYSTEM AND ASSOCIATED INSERTION INSTRUMENTS

The invention relates to a dental implant system comprising an insertion part and an insertion instrument according to the pre-amble of claim 1.

The invention further relates to an insertion instrument forming part of the implant system and being used for tightening the insertion part, and to an auxiliary insertion instrument forming part of the implant system and being used for providing an insertion part, as well as to an associated assembly with package.

Such implant systems are known and are used as a replacement for missing dental elements in people's mouths. This is done by drilling a hole in the jawbone and screwing or pressing the insertion part therein. On the insertion part's neck part projecting from the gums, an abutment, healing cap or similar insertion element is subsequently placed, and at a later point in time, although straightaway is also possible in principle, a dental prosthesis or crown or similar element is placed.

Insertion parts are increasingly manufactured from zirconium oxide-containing material, whether or not stabilised by means of yttrium, in order to preclude disadvantages occurring as a result of the application of titanium insertion parts. Among the advantages are that the gray titanium colour no longer shines through in the gums or that the development of a visible, metal, grey edge of the insertion part in the course of time, when the gums retract further, no longer takes place. In addition, there is reduced occurrence of swelling after surgery, a reduced risk of inflammation and, frequently, less bone resorption.

The insertion parts of two-part dental implants are generally fitted in the jawbone by means of an insertion instrument which is inserted into the recess of the neck part of the insertion part.

International patent application WO 2010/053352 A1 in name of current applicant, discloses an insertion part of a two-part zirconium dental implant according to the opening paragraph, comprising one or more projections on the outer side of the neck part, as well as an insertion instrument with recesses capable of engaging with said projections, allowing the insertion part to be provided in the jawbone by means of a rotary motion, after which it is firmly fixed therein by screwing or tightening.

This implant system yields very good results in terms of a high primary stability, that is to say, a high stability immediately after the screwing operation and before the insertion part and the jawbone grow together, by virtue of the fact that applying a large force of the order of 30 to 45 Ncm to screw the insertion part into the jawbone has proved to be feasible. In turn, this has the advantage that the insertion part can be loaded immediately, on the proviso that the bone quality is sufficient. Other advantages are the substantially reduced risk of complications and the suitability of placing the insertion part directly after the extraction of the original tooth or molar, and the possibility of the insertion part being placed by a general dental practitian or endodontologist without the patient having to be referred to a specialist.

In spite of the above mentioned advantages of the implant system as described hereinabove, it has been found that damage to the insertion part still occurs during the tightening thereof.

It is an object of the invention to provide an improved implant system of the type described hereinabove. The invention particularly aims at providing an improved implant system of the above-described type, wherein the insertion part is not damaged anymore during the tightening operation.

This object is achieved by means of an implant system according to the features of claim 1.

The bridge part encloses the neck part situated next to the projections, such that there is an interspace between bridge part and neck part, as a result of which, when the driving part of the opening embraces the projections of the neck part, contact between said bridge part and said neck part no longer takes place and there is certainly no mechanical load.

The problem of chipping of dental implants, in the prior art, occurs in particular when the implants are made of zirconium oxide, because this material is comparatively brittle as compared to titanium. The neck parts of the insertion parts were tightly embraced by insertion instruments in order to bring the insertion parts to the mouth without contact by the human hand and fix them into the jawbone. Contact with the human hand was avoided in order to preclude contamination of the insertion parts. However, this brought with it that the bridge part of the insertion instrument tightly embraced the neck part, for example because the opening in the bridge part was slightly conical and hence there was no intermediate space. Neck parts which were slightly bevelled or rounded off near the end face thereof were even more prone to said chipping, because such neck parts are very thin and hence extra vulnerable at the location of the bevelled edges or rounded off parts.

In the system according to the invention, such a tight embrace or any other mechanical load is precluded because there is at least some intermediate space.

The presence of intermediate space also brings with it that the insertion instrument is no longer suitable to firmly grip the insertion part, i.e. at least not automatically. This aspect can be solved, for example, by means of an auxiliary insertion instrument by means of which the insertion part can be brought to the mouth and screwed into the jawbone hole to some extent, i.e. at least to the point where the external screw thread of the insertion part engages in the pre-tapped internal screw thread of the jawbone hole, without the insertion part being contacted and hence possibly being contaminated. Subsequently, the auxiliary insertion instrument can be removed from the mouth of the person and the insertion part can be screwed further into the jawbone by means of the insertion instrument and tightened firmly.

The measures according to the characterising part of claim 1 are not obvious to a person skilled in the art, because he will first of all start from the preconception accepted in the art that due to these measures it is no longer possible to bring the insertion part to the mouth without touching it and screw it down to some extent, or only with great difficulty, for example using tweezers.

An embodiment of the dental implant system according to the invention is characterized in that the interspace is such that it remains intact up to an oblique position of approximately 5 degrees of the insertion instrument with respect to the longitudinal axis of the insertion part. As a result thereof, also a limited oblique position of the insertion instrument with respect to the neck part of the insertion part, which may occur during normal manual handling of the insertion instrument, will not cause damage to the neck part.

In another embodiment, the walls of the driving part are prismatic and the bridge part is laterally bounded by one or more walls, which are also prismatic and which are aligned with the walls of the driving part. This embodiment is favourable from a production-technical point of view and is suitable for an insertion part with a neck part which is embodied so as to recede to a limited degree in the proximity of the neck end face, i.e. it narrows in the direction of the neck end face.

In yet another embodiment, the bridge part, with respect to the longitudinal axis of the insertion instrument, is laterally widened with respect to the driving part, in any radial direction with respect to said longitudinal axis. This makes it possible to ensure that there is sufficient intermediate space between the neck part and the bridge part, also in the case of straight, i.e. non-receding, neck parts.

In a further embodiment, the bridge part of the opening of the insertion instrument is contiguous to the driving part, in a non-staggered manner, and widens gradually in an inward direction. In other words, the intermediate space between the neck part and the bridge part increases with the distance to the driving part. By virtue thereof, the intermediate space increases at locations where an increase is required for the purpose of a limited oblique position of the insertion instrument with respect to the insertion part.

Yet another embodiment of the implant system according to the invention comprises an auxiliary insertion instrument for providing the insertion part, which auxiliary insertion instrument is provided with a handle and, connected thereto, a top part which is shaped and dimensioned so as to be suitable to be a tight fit in the recess in the neck part of the insertion part, said top part comprising at least two legs the end portions of which can be resiliently moved towards and away from each other. Advantageously, said top part is made of metal, for example stainless steel.

By implementing said top part, it becomes possible to avoid contact between the insertion part and the human hand or other elements which might cause the insertion part to become contaminated with substances which could lead to inflammation in the patient due to manually providing the insertion part into the mouth of a person. By virtue thereof, it becomes easier to create the sanitary conditions necessary to provide the insertion part, and possibly the associated abutment, into the mouth of a person in a medically sound manner.

The invention further relates to an insertion instrument for screwing down an insertion part of a two-part dental implant.

In an embodiment thereof, the bridge part of the opening is contiguous to the driving part in a non-staggered manner and gradually widens inwards. This makes it possible to ensure that there is sufficient intermediate space also in the case of a straight, i.e. non-receding, neck part of the insertion part.

The invention further relates to an auxiliary insertion instrument for providing an insertion part of a two-part dental implant, comprising a handle and, connected thereto, a top part which is shaped and dimensioned so as to be suitable to be a tight fit in the recess in a neck part of the insertion part, said top part comprising at least two legs the end portions of which can be resiliently moved towards and away from each other. The advantages of such an insertion instrument have already been described hereinabove, in the light of the implant system according to the invention.

Finally, the invention relates to an assembly of an insertion part of a two-part dental implant, an auxiliary insertion instrument, and a package, in which assembly the insertion part is elongated in shape and, viewed in the longitudinal direction, composed of, on the one hand, a screw part, which is provided, over at least part of the length thereof, with an external screw thread, and, on the other hand, a neck part which is located at one of the ends of the insertion part and which comprises a recess in the neck end face thereof which is suitable for fixing an abutment, a healing cap or a similar insertion element, which neck part is provided, at some distance from the neck end face, with one or more projections which are situated at the circumference of the neck and which extend in the radial direction, which insertion part is made entirely or substantially entirely of zirconium oxide-containing material, the auxiliary insertion instrument is provided, with the top part thereof, in the recess of the neck part of the insertion part, and the package forms an envelope of the insertion part and the auxiliary insertion instrument, which package seals the insertion part and the auxiliary insertion instrument so as to ensure the sterility thereof.

By means of such an assembly, after the insertion part according to the invention has been packed and sterilized, it becomes easier to store said insertion part for a prolonged period of time, transport said insertion part and provide it into the jawbone of a person at some point in time, in a medically sound manner, i.e. in any case without touching it with the human hand and avoiding other possible sources of contamination.

The invention will now be explained in greater detail with reference to the accompanying drawings, in which corresponding parts are indicated by means of the same reference numerals.

FIG. 3a is a side view of the insertion instrument shown in FIG. 1; FIG. 3b is a cross-sectional view of this insertion instrument taken on the line A-A in FIG. 3a, and FIG. 3c is a longitudinal sectional view of the socket part of this insertion instrument.

FIG. 4a is a side view of an auxiliary insertion instrument according to the invention, and FIG. 4b shows an end view of this auxiliary instrument accommodating the top part.

Figure 1B:
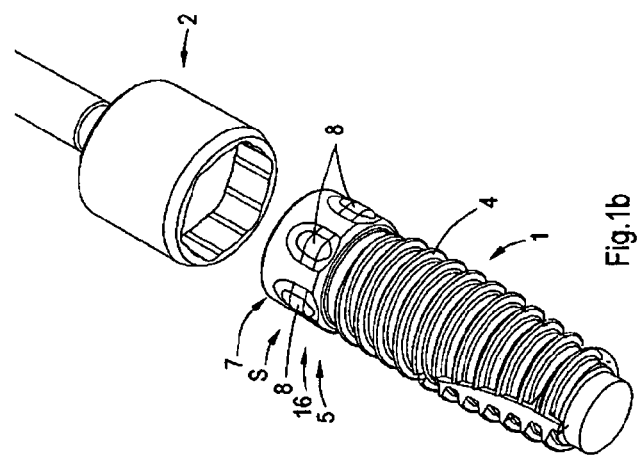
FIG. 1b shows a similar perspective view of the system shown in FIG. 1a, in which the insertion instrument is in line with the insertion part.
Figure 1A:
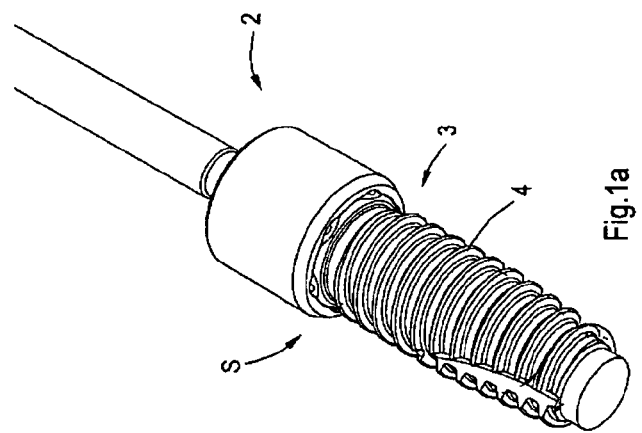
FIG. 1a shows a perspective view of an embodiment of an implant system according to the invention, in which the insertion instrument is positioned over the insertion part.
Figure 2A:
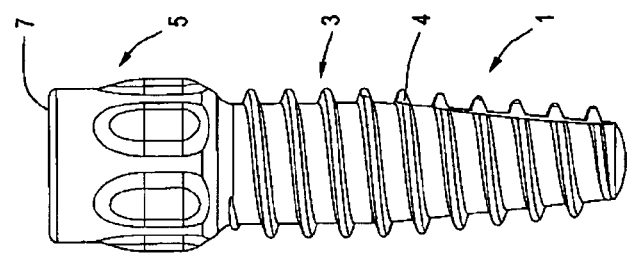
FIGS. 2a and 2b are two longitudinal sectional views of the insertion part shown in FIG. 1.
Figure 2B:
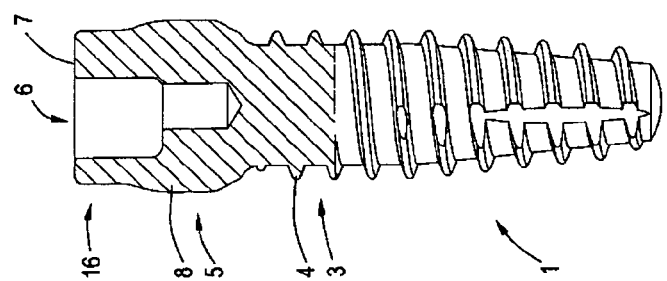
Figure 2C:
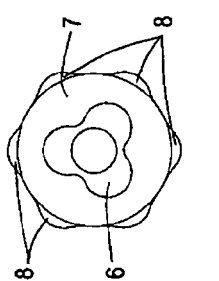
FIG. 2c is an elevational view of the neck end face of this insertion part.

FIG. 1a shows a two-part dental implant system S comprising an elongated insertion part 1 and an insertion instrument 2. As is also shown in FIG. 2a and FIG. 2b, the insertion part 1 is, viewed in the longitudinal direction, composed of, on the one hand, a screw part 3 with external screw thread 4, and, on the other hand, a neck part 5 which is located at one end of the insertion part 1 and which comprises a recessed portion 6 (see FIG. 2b and FIG. 2c) in the neck end face 7 thereof which is suitable for fixing an abutment. The neck part 5 is provided, at some distance from the neck end face 7, with one or more projections 8 which are situated at the circumference of the neck and which extend in the radial direction. Between the neck end face 7 and the projections 8, the diameter is slightly reduced as compared to the smallest diameter at the level of the projections 8. In this exemplary embodiment, the insertion part 1 is entirely made of zirconium oxide-containing ceramic stabilised with yttrium, although, according to the invention, other zirconium-containing materials are also possible.

The insertion instrument 2, shown in greater detail in FIG. 3a, comprises an elongated handle part 9 which ends in a socket part 10 having a socket end face 11 extending perpendicularly to the longitudinal axis of the handle part 9. The socket part 10 has an opening 12 which terminates at the socket end face 11, see FIGS. 3b and 3c, which opening 12 has a driving part 13 and a bridge part 14 contiguous to said driving part 13 on the side of the driving part 13 facing towards the inside of the opening 12, i.e. the side facing the handle part 9 and facing away from the socket end face 11. In the driving part 13, the opening 12 is laterally bounded by walls and has a cross-section at right angles to the longitudinal axis L (see FIGS. 3a and 3c), which is substantially hexagonal, i.e. not circular, and the shape and dimensions of which are suitable to at least partly accommodate the neck part 5 of the insertion part (as is shown in FIG. 1a and FIG. 1b), and to transfer the tightening torque applied to the handle part 9 to the insertion part 1 through said six projections 8 situated around the neck.

In the embodiment shown, the bridge part has the shape of a truncated round cone, i.e. a diameter which increases inwards in the opening 12, that is, in a direction away from the socket end face, and is contiguous to the driving part, in a substantially non-staggered manner. As a result of said conical shape, when the driving part 13 of the opening having six recessed portions embraces the projections of the neck part, the bridge part 14 encloses the neck part 16 (also see FIG. 1b and FIG. 2b for the neck part) situated next to the projections 8 and extending up to the neck end face, such that there is an interspace between said bridge part and said neck part.

In this exemplary embodiment, the intermediate space can be attributed to, on the one hand, the slightly reduced diameter of the neck part 5 between the neck end face 7 and the projections 8 and, on the other hand, the increase of the diameter in the bridge part 14 in the direction of the handle part 9. Each of these two measures can be applied separately, but in this exemplary embodiment, both measures are applied jointly, so that in all situations, including an occasionally occurring oblique position of the insertion instrument with respect to the insertion part up to approximately 5 degrees, an interspace remains between, on the one hand, the neck part 5 from the neck end face 11 to the projections 8 and, on the other hand, the bridge part 14. In this exemplary embodiment, the walls of the driving part 13 are substantially prismatic for, inter alia, enabling the insertion instrument to be provided on and removed from the projections 8 in a simple manner. In this exemplary embodiment, the depth of the opening 12 is such that the socket part 10 exactly encloses the entire neck part 5 of the insertion part 1 when said neck part 5 is pressed with the neck end face thereof against the end of the opening 12.

In an exemplary embodiment (not shown), the bridge part is laterally widened, with respect to the longitudinal axis of the insertion instrument, relative to the driving part, in any radial direction with respect to said longitudinal axis, i.e. already at the transition from driving part to bridge part. In this manner an intermediate space is ensured also when insertion parts are used which are not reduced in size close to the neck end face.

FIG. 4a shows an auxiliary insertion instrument 17 pertaining to the implant system shown in FIGS. 1 to 3, and being used for providing the insertion part 1. The auxiliary insertion instrument 17 is provided with a handle 18 and a top part 19 which, in this exemplary embodiment, is integral with the handle 18. Said top part comprises three resilient legs 20. The auxiliary insertion instrument 17 is made of stainless steel and the legs 20 are shaped so as to be so thin that they can resiliently move towards the longitudinal axis of the auxiliary insertion instrument 17 and hence also towards one another and away from one another. The top ends 21 of the legs 20 are, in addition, slightly rounded off and smooth to prevent damage to the insertion part 1 when they are inserted into the opening 6 of said insertion part. In addition, by virtue of said rounded off shape of the top ends 21 of the legs 20, the legs 20 resiliently move towards each other when the top part 19 is provided into the opening of the insertion part 1. Next to the top ends, in a direction more towards the handle 18, said legs 20 have outer walls 22 which are jointly parallel to the longitudinal axis of the auxiliary insertion instrument 17, and next thereto, even more towards the handle 18, the legs 20 jointly have an outer diameter which becomes smaller in a direction towards the handle 18. Said rounded off shape of the top ends and the parallel outer walls 22 and shrinking diameters make it possible to insert the legs 20 into the opening 6 of the insertion part 1 so as to be a tight fit therein, by pressing the auxiliary insertion instrument 17 in a simple manner and without further tools into the opening 6 of the insertion part 1. Subsequently, the insertion part 1 can be retained, supported and moved using only the auxiliary insertion instrument 17.

It is not shown in the Figures that, while the top part 20 is inserted into the opening 6, the auxiliary insertion instrument 17 and the insertion part 1 are jointly packed in a package consisting of a substantially cylindrical glass tube with a reclosable cover of metal, which package does not comprise synthetic resin elements nor other contaminating substances. In use, the package containing the auxiliary insertion instrument 17 and the insertion part 1 is sterilized, after which it is transported, stored and used for providing, in a medically sound as well as easy manner, the insertion part 1 into the pre-treated jawbone of a person and tightening it to some degree.

Variants are possible to the exemplary embodiment described hereinabove, which fall within the scope of the invention as defined in the claims. For example, fewer or more than six projections 8 may be provided.

The invention claimed is:

1. A dental implant system comprising:
   an insertion part of a two-part dental implant, which insertion part is elongated in shape and, viewed in the longitudinal direction, includes a screw part provided over at least part of the length thereof, with an external screw thread, and a neck part located at one of ends of the insertion part and which comprises a recess in a neck end face thereof configured to fix an abutment, a healing cap, or an insertion element,
   wherein the neck part is provided at some distance from the neck end face, with one or more projections situated at the circumference of the neck and which extend in the radial direction, and
   wherein the insertion part is made entirely or substantially entirely of zirconium oxide-containing material;
   further comprising an insertion instrument for screwing down the insertion part of the two-part dental implant, which insertion instrument comprises a drivable elongated handle part which ends in a socket part having a socket end face extending substantially perpendicularly to the longitudinal axis of the handle part,
   wherein the socket part includes an opening which terminates at the socket end face, and at least the driving part of which is laterally bounded by one or more walls, which driving part of the opening has a cross-section at right angles to the longitudinal axis, which cross-section is not circular and a shape and dimensions of which are suitable to at least partly accommodate the neck part of the insertion part, and to transfer tightening torque applied to the handle part to the insertion part through the projections, wherein the opening of the insertion instrument includes a bridge part contiguous to a side of the driving part facing towards an inside of the opening, and wherein the bridge part encloses the neck part situated next to the projections and extending up to the neck end face, such that there is an interspace between the bridge part and the neck part, when the driving part of the opening embraces the projections of the neck part; and further comprising an auxiliary insertion instrument for providing the insertion part, which auxiliary insertion instrument includes a handle and, connected thereto, a top part shaped and dimensioned to be a tight fit in a recess in the neck part of the insertion part, the top part comprising at least two legs with end portions which can be resiliently moved towards and away from each other.

2. The dental implant system according to claim 1, wherein the interspace is sized such that it remains intact up to an oblique position of approximately 5 degrees of the insertion instrument with respect to the longitudinal axis of the insertion part.

3. The dental implant system according to claim 1, wherein the walls of the driving part are prismatic and the bridge part is laterally bounded by one or more walls, which are also prismatic and which are aligned with the walls of the driving part.

4. The dental implant system according to claim 1, wherein, with respect to the longitudinal axis of the insertion instrument, the bridge part is laterally widened with respect to the driving part, in any radial direction with respect to the longitudinal axis.

5. The dental implant system according to claim 1, wherein the bridge part of the opening of the insertion instrument is contiguous to the driving part, in a non-staggered manner, and widens gradually in an inward direction.

6. The dental implant system according to claim 1, wherein the top part is made of metal.

* * * * *